(12) United States Patent
Niver

(10) Patent No.: US 12,023,075 B2
(45) Date of Patent: Jul. 2, 2024

(54) BONE FIXATION SYSTEMS AND METHODS FOR FIXATING BONES

(71) Applicant: Ryan J. Niver, Glenview, IL (US)

(72) Inventor: Ryan J. Niver, Glenview, IL (US)

(*) Notice: Subject to any disclaimer, the term of this patent is extended or adjusted under 35 U.S.C. 154(b) by 157 days.

(21) Appl. No.: 17/700,071

(22) Filed: Mar. 21, 2022

(65) Prior Publication Data

US 2023/0293211 A1 Sep. 21, 2023

(51) Int. Cl.
*A61B 17/80* (2006.01)
*A61B 17/88* (2006.01)
*A61B 17/00* (2006.01)
*A61B 17/70* (2006.01)

(52) U.S. Cl.
CPC .......... *A61B 17/8004* (2013.01); *A61B 17/80* (2013.01); *A61B 17/8019* (2013.01); *A61B 17/808* (2013.01); *A61B 17/88* (2013.01); *A61B 2017/00867* (2013.01); *A61B 17/7059* (2013.01)

(58) Field of Classification Search
CPC .......... A61B 17/0642; A61B 17/7059; A61B 17/8004; A61B 17/8019; A61B 17/808; A61B 17/88; A61B 17/8863; A61B 17/8872
See application file for complete search history.

(56) References Cited

U.S. PATENT DOCUMENTS

| | | |
|---|---|---|
| 3,866,607 A | 2/1975 | Forsythe et al. |
| 5,423,826 A | 6/1995 | Coates et al. |
| 5,785,713 A | 7/1998 | Jobe |
| 7,115,129 B2 * | 10/2006 | Heggeness ........... A61B 17/808 606/279 |
| 7,338,527 B2 | 3/2008 | Blatt et al. |
| 7,727,259 B2 | 6/2010 | Park |
| 8,083,781 B2 | 12/2011 | Reimels et al. |
| 8,172,886 B2 | 5/2012 | Castaneda et al. |
| 8,211,145 B2 | 7/2012 | Dalton |
| 8,211,476 B2 | 7/2012 | Kanamaru et al. |
| 8,231,680 B2 | 7/2012 | Bullard |
| 8,246,664 B2 | 8/2012 | Terrill et al. |
| 8,574,270 B2 | 11/2013 | Hess et al. |
| 8,974,504 B2 | 3/2015 | Hess et al. |
| 9,005,251 B2 | 4/2015 | Heggeness |

(Continued)

FOREIGN PATENT DOCUMENTS

WO WO-2009091770 A1 * 7/2009 ......... A61B 17/0642
WO 2017190236 A1 11/2017

*Primary Examiner* — Larry E Waggle, Jr.
(74) *Attorney, Agent, or Firm* — von Briesen & Roper, s.c.

(57) ABSTRACT

Bone fixation systems and methods include a surgical plate formed of a shape memory material, and an insertion tool for bending the plate. Receptacles are formed in the plate inwardly of an outer periphery. The plate further includes a body central portion located inwardly of the outer periphery, disposed between the first and second receptacles. The insertion tool includes first and second arms configured to engage the receptacles, and a rod disposed between the arms and configured to engage the body central portion. The rod is movable between a first rod position, in which the surgical plate has the initial shape, and a second rod position, in which the rod engages and displaces the plate body central portion so that the surgical plate has the flexed shape. In some embodiments, the insertion tool may be operated to modify a length of the surgical plate.

20 Claims, 13 Drawing Sheets

(56) References Cited

U.S. PATENT DOCUMENTS

| | | |
|---|---|---|
| 9,381,044 B2 | 7/2016 | Robinson et al. |
| 9,532,819 B2 | 1/2017 | Campbell |
| 9,724,132 B2 | 8/2017 | Gamache et al. |
| 9,839,457 B2 | 12/2017 | Williams |
| 9,872,681 B2 | 1/2018 | Miller et al. |
| 9,883,897 B2 | 2/2018 | Taber |
| 9,924,987 B2 | 3/2018 | Cheney |
| 10,022,160 B2 | 7/2018 | Robinson et al. |
| 10,076,365 B2 | 9/2018 | Bullard |
| 10,292,743 B2 | 5/2019 | Taylor et al. |
| 10,327,914 B2 | 6/2019 | Arlet |
| 10,376,380 B2 | 8/2019 | Gamache et al. |
| 10,492,841 B2 * | 12/2019 | Hartdegen ......... A61B 17/8061 |
| 10,842,487 B2 | 11/2020 | Ritz et al. |
| 10,918,484 B2 | 2/2021 | Ellington et al. |
| 11,000,323 B2 | 5/2021 | Stamp et al. |
| 11,006,949 B2 | 5/2021 | Daniel |
| 11,202,626 B2 | 12/2021 | Hartdegen et al. |
| 2004/0215192 A1 | 10/2004 | Justis et al. |
| 2006/0189989 A1 | 8/2006 | Bert et al. |
| 2007/0239158 A1 | 10/2007 | Trieu et al. |
| 2008/0039847 A1 | 2/2008 | Piper et al. |
| 2015/0230843 A1 | 8/2015 | Palmer et al. |
| 2016/0354126 A1 | 12/2016 | Nayet et al. |
| 2018/0263673 A1 | 9/2018 | Mazzola et al. |
| 2019/0000513 A1 | 1/2019 | Bullard |
| 2019/0110824 A1 * | 4/2019 | Kobayashi ......... A61B 17/8085 |
| 2019/0150921 A1 * | 5/2019 | Fonte ................. A61B 17/0684 |
| 2020/0222091 A1 | 7/2020 | Palmer et al. |
| 2021/0378722 A1 | 12/2021 | Taylor et al. |
| 2023/0225774 A1 | 7/2023 | Lui et al. |

* cited by examiner

BONE FIXATION SYSTEMS AND METHODS FOR FIXATING BONES

BACKGROUND

Technical Field

The present disclosure generally relates to surgical devices, and more particularly to systems and methods of fixating bones with plates.

Description of the Related Art

Surgical plates for fixating bones and applying compression are generally known. In recent years, forming the surgical plate out of shape memory material has been proposed. Known methods for fixating such surgical plates to bone have proven to be overly difficult to execute. Furthermore, known bone fixation systems that employ surgical plates formed of shape memory material are constrained to only one mode of modifying the shape of the surgical plate.

SUMMARY OF THE DISCLOSURE

In accordance with one aspect of the present disclosure, a bone fixation system, comprises a surgical plate formed of a shape memory material. The surgical plate includes a plate body spanning a length along a longitudinal axis, a width along a lateral axis perpendicular to the longitudinal axis, and a thickness along a vertical axis orthogonal to both the longitudinal axis and the lateral axis, and the plate body defines a plate outer periphery. The surgical plate further includes a first receptacle located inwardly of the plate outer periphery, a second receptacle located inwardly of the plate outer periphery and spaced from the first receptacle, and a plate body central portion located inwardly of the plate outer periphery and disposed between the first and second receptacles. The bone fixation system further includes an insertion tool having a first arm configured to engage first receptacle, a second arm configured to engage the second receptacle, and a rod disposed between first and second arms and configured to engage the plate body central portion, the rod supported for movement along the vertical axis. With the first arm of the insertion tool engaging the first receptacle of the surgical plate and the second arm of the insertion tool engaging the second receptacle of the surgical plate, the rod of the insertion tool is movable along the vertical axis between a first rod position, in which the surgical plate has an initial shape, and a second rod position, in which the rod engages and displaces the plate body central portion so that the surgical plate has a flexed shape different from the initial shape.

In accordance with another aspect of the present disclosure, a method for fixating bone includes providing a surgical plate formed of a shape memory material. The surgical plate comprises a plate body spanning a length along a longitudinal axis, a width along a lateral axis perpendicular to the longitudinal axis, and a thickness along a vertical axis orthogonal to both the longitudinal axis and the lateral axis, the plate body defining a plate outer periphery. The surgical plate further includes a first receptacle located inwardly of the plate outer periphery, a second receptacle located inwardly of the plate outer periphery and spaced from the first receptacle, and a plate body central portion located inwardly of the plate outer periphery and disposed between the first and second receptacles. The method further includes providing an insertion tool that includes a first arm configured to engage the first receptacle, a second arm configured to engage the second receptacle, and a rod disposed between first and second arms and configured to engage the plate body central portion, the rod supported for movement along the vertical axis. The method also includes engaging the first arm of the insertion tool with the first receptacle of the surgical plate, engaging the second arm of the insertion tool with the second receptacle of the surgical plate, and moving the rod along the vertical axis from a first rod position, in which the surgical plate has an initial shape, to a second rod position, in which the rod engages and displaces the plate body central portion so that the surgical plate has a flexed shape different from the initial shape. Still further, the method includes positioning the surgical plate, while in the flexed shape, adjacent the bone, securing the surgical plate to the bone with fasteners, and moving the rod along the vertical axis from the second rod position to the first rod position, so that the shape memory material causes the surgical plate to apply compression to the bone.

In accordance with yet another aspect of the present disclosure, a bone fixation system comprises a surgical plate formed of nitinol. The surgical plate comprises a plate body spanning a length along a longitudinal axis, a width along a lateral axis perpendicular to the longitudinal axis, and a thickness along a vertical axis orthogonal to both the longitudinal axis and the lateral axis, the plate body defining a plate outer periphery, a first receptacle located inwardly of the plate outer periphery, a second receptacle located inwardly of the plate outer periphery and spaced from the first receptacle, and a plate body central portion located inwardly of the plate outer periphery and disposed between the first and second receptacles. The bone fixation system further includes an insertion tool having a first arm configured to engage first receptacle, a second arm configured to engage the second receptacle, and a rod disposed between first and second arms and configured to engage the plate body central portion, the rod supported for movement along the vertical axis. With the first arm of the insertion tool engaging the first receptacle of the surgical plate and the second arm of the insertion tool engaging the second receptacle of the surgical plate, the rod of the insertion tool is movable along the vertical axis between a first rod position, in which the surgical plate has an initial shape, and a second rod position, in which the rod engages and displaces the plate body central portion so that the surgical plate has a flexed shape different from the initial shape. Additionally, the first arm is movable relative to the second arm along the longitudinal axis between a first position, in which the first arm and the second arm are separated by a first longitudinal distance, and a second position, in which the first and second arm are separated by a second longitudinal distance that is less than the first longitudinal distance. Still further, with the first arm of the insertion tool engaging the first receptacle and the second arm of the insertion tool engaging the second receptacle, the surgical plate has a first length when the first arm is in the first position, and a second length, less than the first length, when the first arm is in the second position.

BRIEF DESCRIPTION OF THE DRAWINGS

For a more complete understanding of the disclosed methods and apparatus, reference should be made to the embodiment illustrated in greater detail on the accompanying drawings, wherein.

It should be understood that the drawings are not necessarily to scale and that the disclosed embodiments are sometimes illustrated diagrammatically and in partial views. In certain instances, details which are not necessary for an understanding of the disclosed methods and apparatus or which render other details difficult to perceive may have been omitted. It should be understood, of course, that this disclosure is not limited to the particular embodiments illustrated herein.

DETAILED DESCRIPTION

Apparatus and methods are described herein for applying compression to a bone. In particular, a surgical plate formed of a shape memory material is deflected from an initial shape to a flexed shape by an insertion tool prior to attachment to the bone. The insertion tool may apply a three point bend to the plate to place the plate in the flexed shape. Additionally or alternatively, the insertion tool may stretch or compress the plate in a longitudinal direction. After attachment of the plate to the bone, the plate is released from the insertion tool. Upon release, the plate seeks to return to the initial state, thereby applying compression to the bone. The apparatus and methods disclosed herein advantageously permit use of an insertion tool that engages the surgical plate inside an outer periphery of the plate. Additionally, certain embodiments disclosed herein allow both bending of the surgical plate as well as modifying a length of the surgical plate prior to fixating the surgical plate to bone.

FIGS. 1-10 illustrate a first example of a bone fixation system 100 and method according to the present disclosure. The bone fixation system 100 generally includes a surgical plate 102 and an insertion tool 103. The surgical plate 102 formed of a shape memory material. The shape memory material may be any material that can be deformed from an initial shape to a flexed shape upon application of external forces, but that seeks to recover the initial shape upon release of the external forces. In some examples, the shape memory material used for the surgical plate 102 is nitinol, however other shape memory materials may be used.

Figure 1:
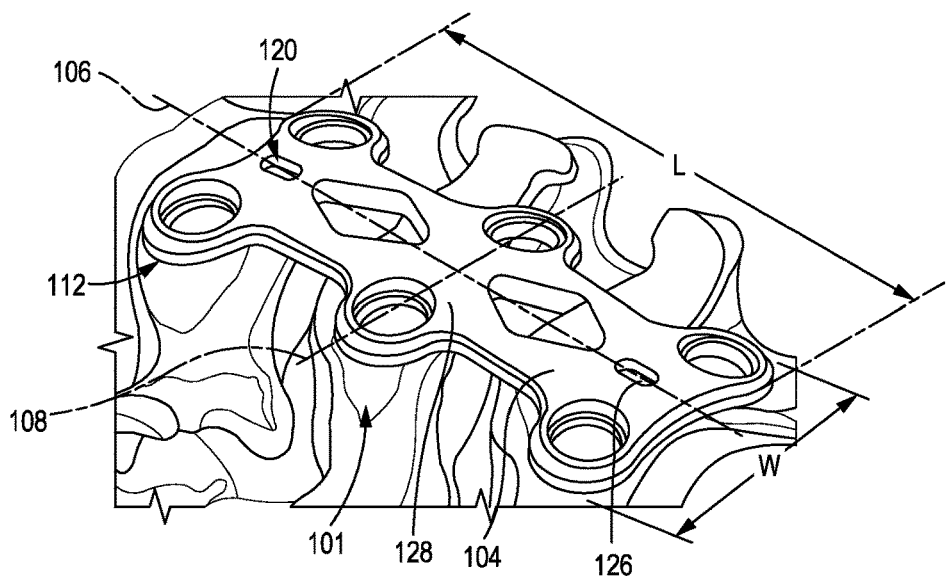
FIG. 1 is a perspective view of a surgical plate, according to the present disclosure, attached to bone.
Figure 2:
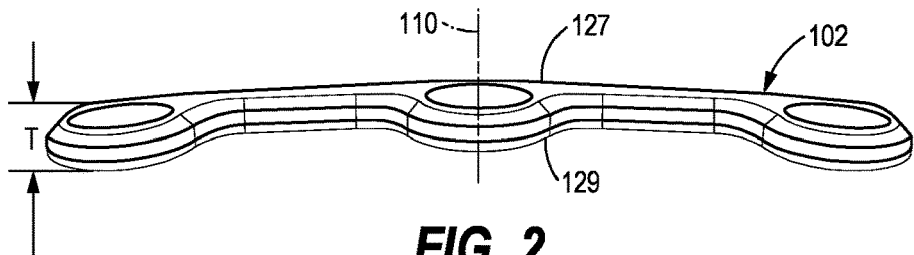
FIG. 2 is a side elevation view of the surgical plate of FIG. 1.

The surgical plate 102 includes a plate body 104. As best shown in FIGS. 1 & 2, the plate body 104 spans a length L along a longitudinal axis 106, a width W along a lateral axis 108 that is perpendicular to the longitudinal axis 106, and a thickness T along a vertical axis 110 orthogonal to both the longitudinal axis 106 and the lateral axis 108. The plate body 104 further defines a plate outer periphery 112 which defines the outer margins of the surgical plate 102 in the longitudinal and lateral axes 106, 108, respectively.

Figure 5:
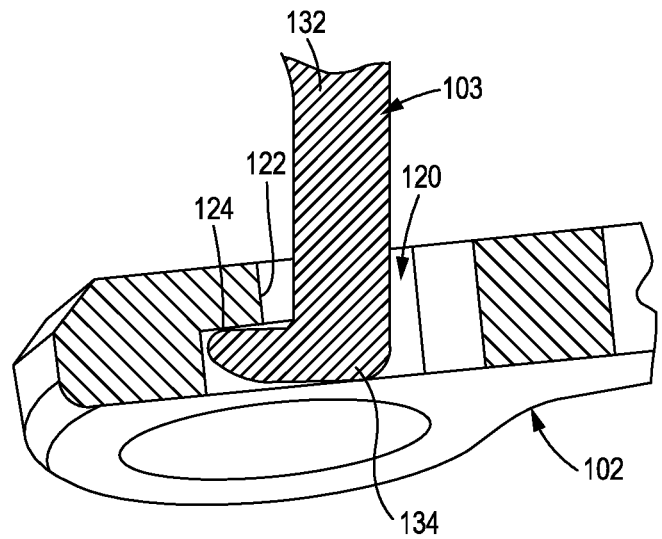
FIG. 5 is an enlarged side elevation view, in cross-section, of the bone fixation system of FIG. 3, with an arm of the insertion tool engaging a receptacle of the surgical plate.

The surgical plate 102 includes areas for selective engagement with the insertion tool 103. As best shown in FIGS. 1 and 5, the surgical plate 102 includes a first receptacle 120 located inwardly of the plate outer periphery 112 and defining a first engagement point for the insertion tool 103. In the illustrated example, the first receptacle 120 comprises a through-hole 122 defining a shoulder 124. The surgical plate also includes a second receptacle 126, spaced from the first receptacle 120, which is located inwardly of the plate outer periphery 112 and defines a second engagement point for the insertion tool 103. The second receptacle 126 may also comprise a through-hole defining a shoulder, similar to the first receptacle 120. In this example, the first and second receptacles 120, 126 are formed as dedicated first and second slots, respectively, that are formed in the surgical plate 102 specifically to permit engagement with the insertion tool 103.

Still further, the surgical plate 102 includes a plate body central portion 128 located inwardly of the plate outer periphery 112 and disposed between the first and second receptacles 120, 126, the plate body central portion 128 defining a third engagement point for the insertion tool 103. The plate body central portion 128 defines an outward surface 127 and an inward surface 129 opposite the outward surface and facing bone 101.

The insertion tool 103 engages and manipulates the surgical plate 102 as the surgical plate 102 is fixed to bone 101. As illustrated in FIGS. 3-8, the insertion tool 103 includes a chassis 130. A first arm 132 is coupled to the chassis 130, and includes a first arm end 134 configured to engage the first receptacle 120. More specifically, as best shown in FIG. 5, the first arm 132 is sized to pass through the through-hole 122, and the first arm end 134 is configured to engage the shoulder 124 of the first receptacle 120. The insertion tool 103 also includes a second arm 136 coupled to the chassis 130 configured to engage the second receptacle 126. While not illustrated separately, the second arm 136 may engage the second receptacle 126 in a manner similar to how the first arm 132 engages the first receptacle 120. In the illustrated example, each of the first and second arms 132, 136 is a rigid, structural component. The insertion tool 103 further includes a rod 140 coupled to the chassis 130 and disposed between first and second arms 132, 136. As explained in greater detail below, the rod 140 is supported for movement along the vertical axis 110, and is configured to engage the plate body central portion 128.

The insertion tool 103 may be used to apply a three-point bend on the surgical plate 102, thereby to move the surgical plate 102 from an initial shape to a flexed shape. More specifically, with the first arm 132 of the insertion tool 103 engaging the first receptacle 120 of the surgical plate 102, and with the second arm 136 of the insertion tool 103 engaging the second receptacle 126 of the surgical plate 102, the rod 140 of the insertion tool 103 may be moved along the vertical axis 110 between a first rod position illustrated in FIG. 3, in which the rod 140 does not engage the surgical plate 102 and the surgical plate 102 has an initial shape (FIG. 2), and a second rod position illustrated in FIG. 4, in which the rod engages and displaces the plate body central portion 128 so that the surgical plate 102 has a flexed shape (FIG. 4) different from the initial shape. In this example, the rod 140 may be threadably coupled to the chassis 130. A knob 142 (FIG. 3) coupled to the rod 140 allows a user to manually rotate the rod 140, thereby to move the rod 140 along the vertical axis 110. In the example illustrated in FIGS. 1-9, the insertion tool 103 is configured so that the rod 140 engages the outward surface 127 of the plate body central portion 128.

Figure 3:
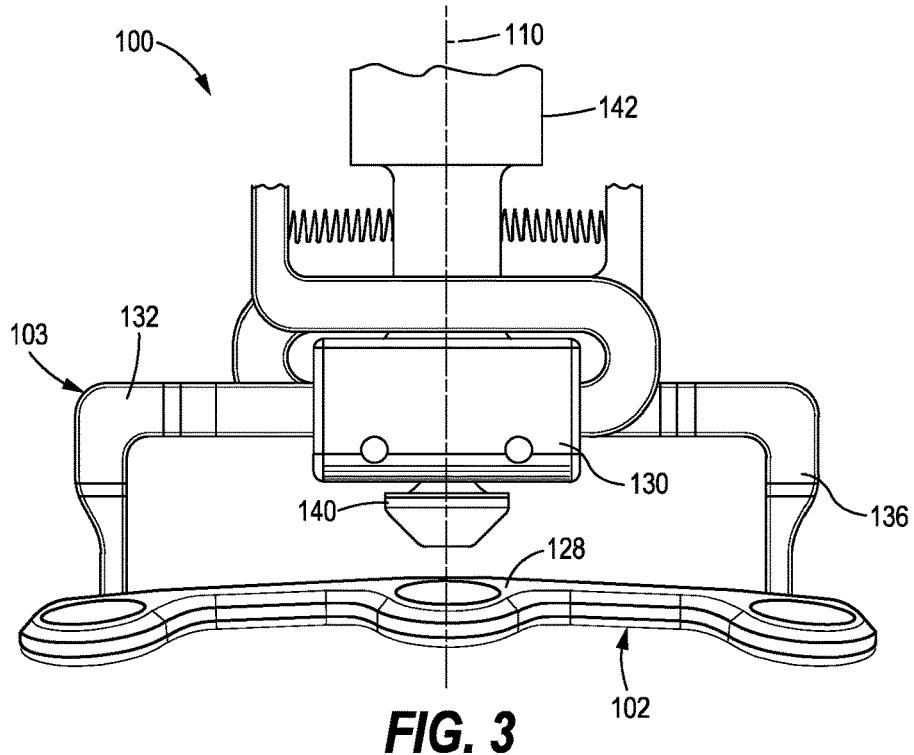
FIG. 3 is a side elevation view of a bone fixation system, including the surgical plate of FIG. 1 and an insertion tool, according to the present disclosure, with the surgical plate in an initial shape.
Figure 4:
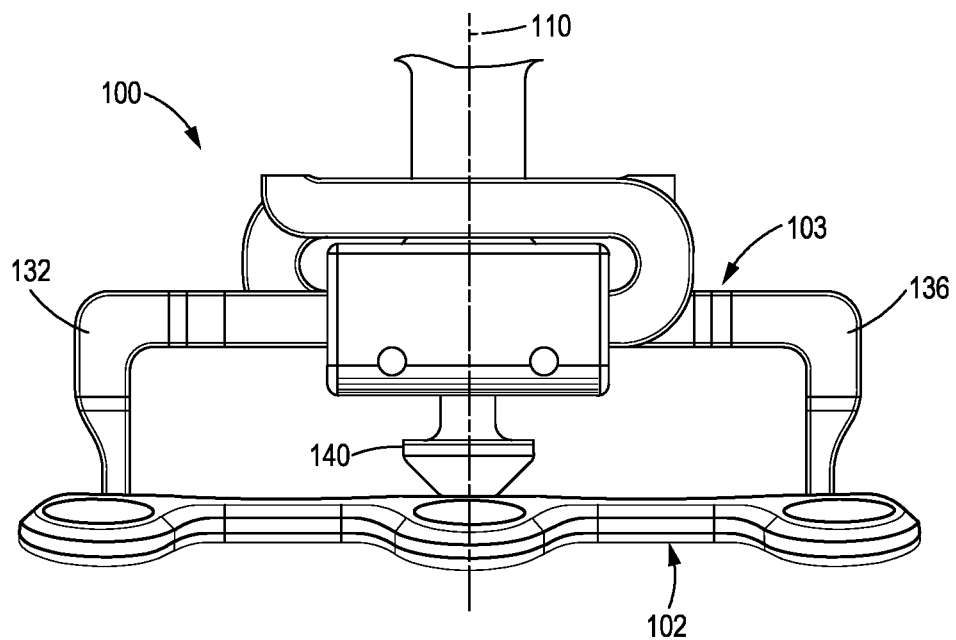
FIG. 4 is a side elevation view of the bone fixation system of FIG. 3, with a rod of the insertion tool in a first position spaced from the surgical plate, and with the surgical plate in a flexed shape.

FIGS. 3-10 illustrate a method 180 for fixating bone 101. The method 180 includes, at block 182, providing the surgical plate 102 described above and, at block 184, providing the insertion tool 103 described above. The method 180 continues with block 186, in which the first arm 132 of the insertion tool 103 is placed into engagement with the first receptacle 120 of the surgical plate 102 and the second arm 136 of the insertion tool 103 is placed into engagement with the second receptacle 126 of the surgical plate, as shown in FIG. 3. At block 188, the method continues by moving the rod 140 along the vertical axis 110 from a first rod position, in which the surgical plate 102 has an initial shape, to a second rod position, in which the rod 140 engages and displaces the plate body central portion 128 so that the surgical plate 102 has a flexed shape different from the initial shape, as best shown in FIG. 4.

Figure 6:
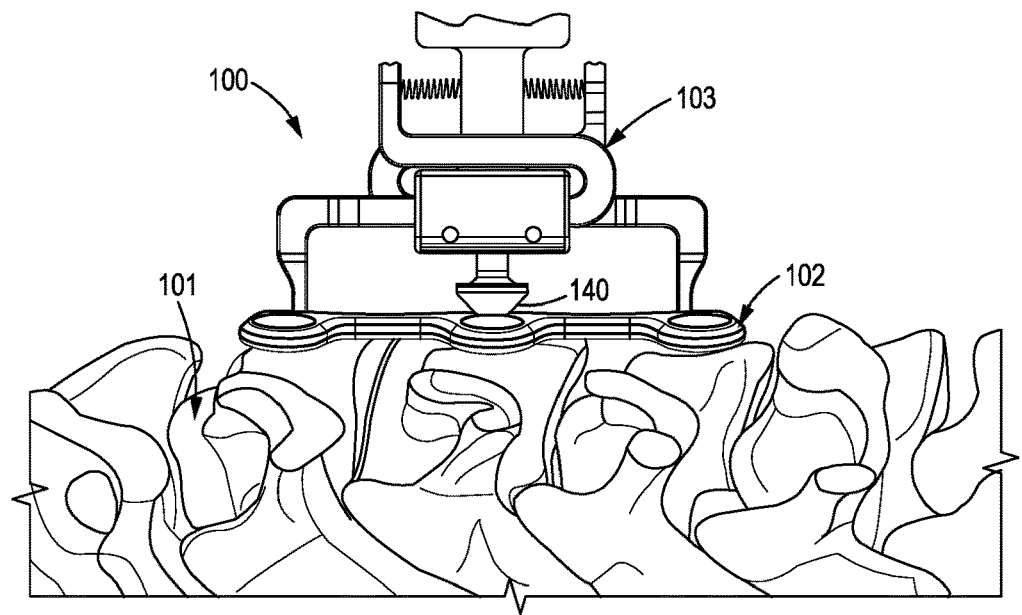
FIG. 6 is a side elevation view of the bone fixation system of FIG. 3, with the rod of the insertion tool in a second position that engages and deforms the surgical plate to a flexed shape.
Figure 7:
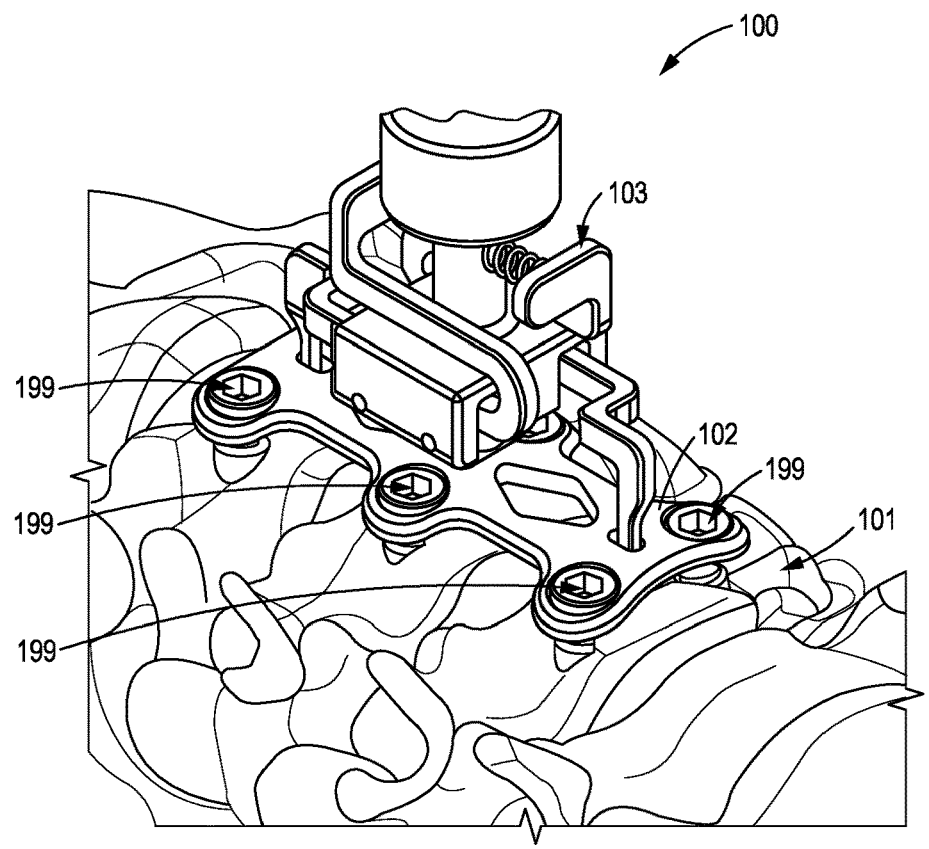
FIG. 7 is a perspective view of the bone fixation system of FIG. 3, showing fasteners attaching the surgical plate to the bone.
Figure 8:
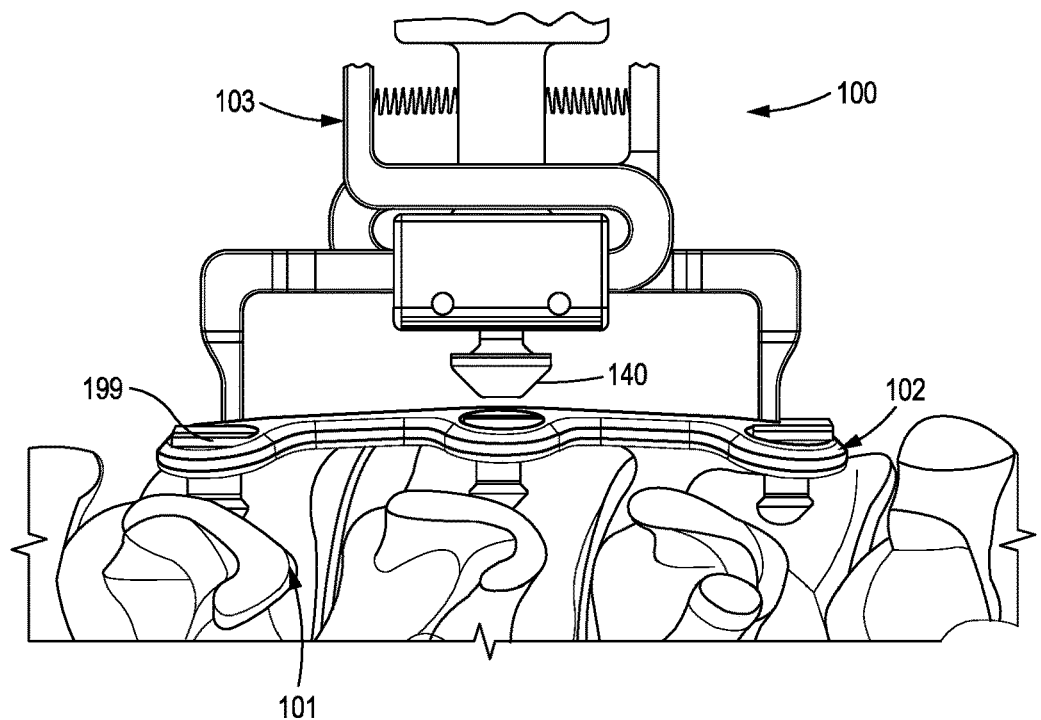
FIG. 8 is a side elevation view of the bone fixation system of FIG. 3, with the rod of the insertion tool returned to the first position while the surgical plate is fixed to the bone.
Figure 9:
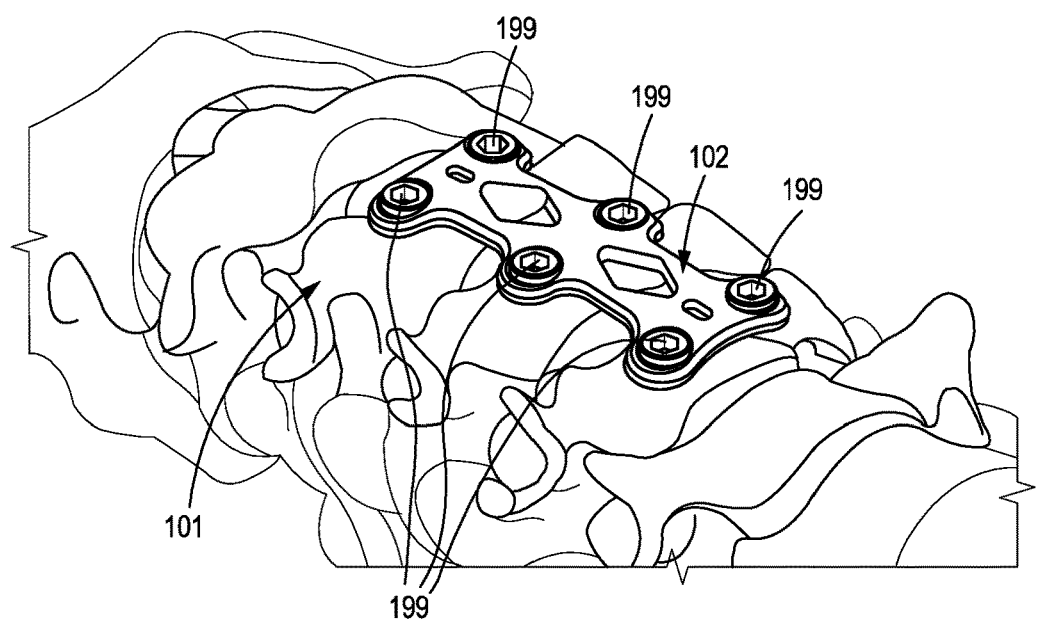
FIG. 9 is a perspective view of the surgical plate fixed to the bone and the insertion tool removed.
Figure 10:
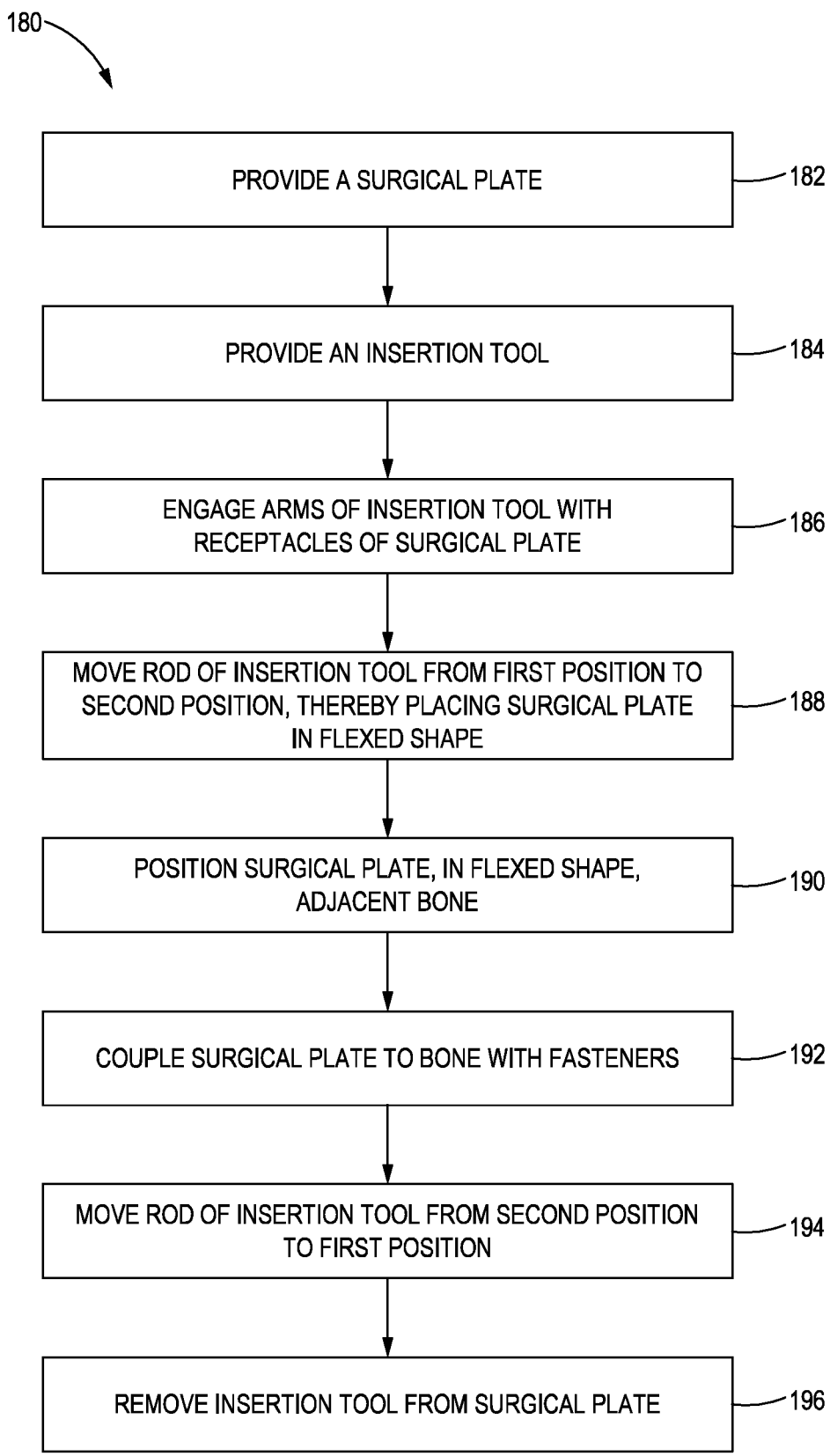
FIG. 10 is a block diagram of a method of fixating bone using the bone fixation system of FIG. 3.
Figure 11:
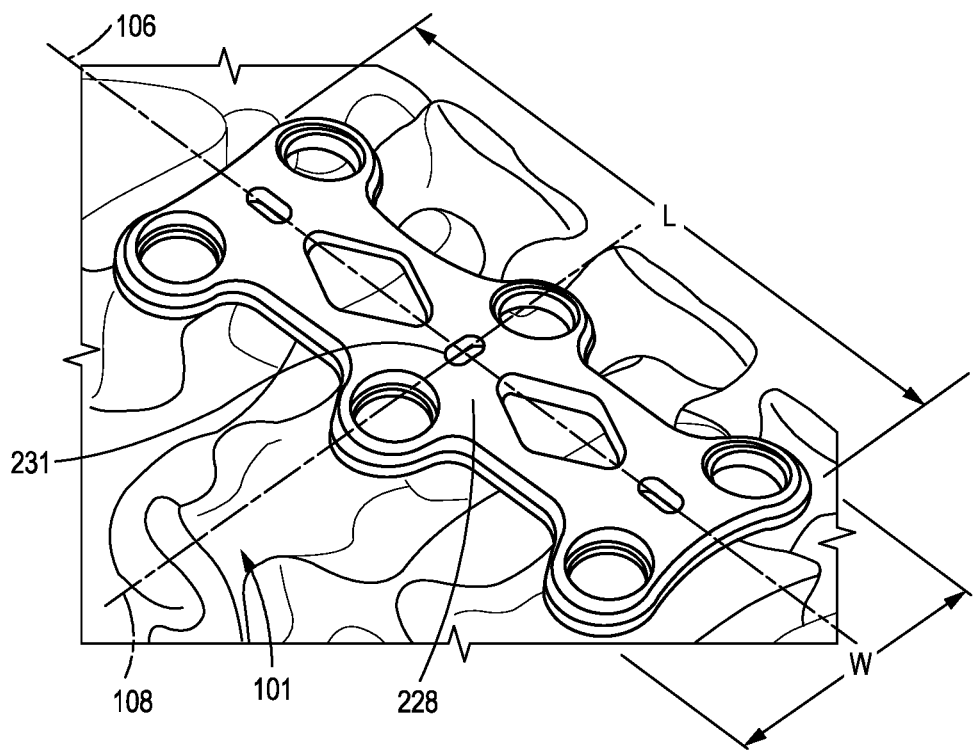
FIG. 11 is a perspective view of a second example of a surgical plate, according to the present disclosure, attached to bone.
Figure 12:
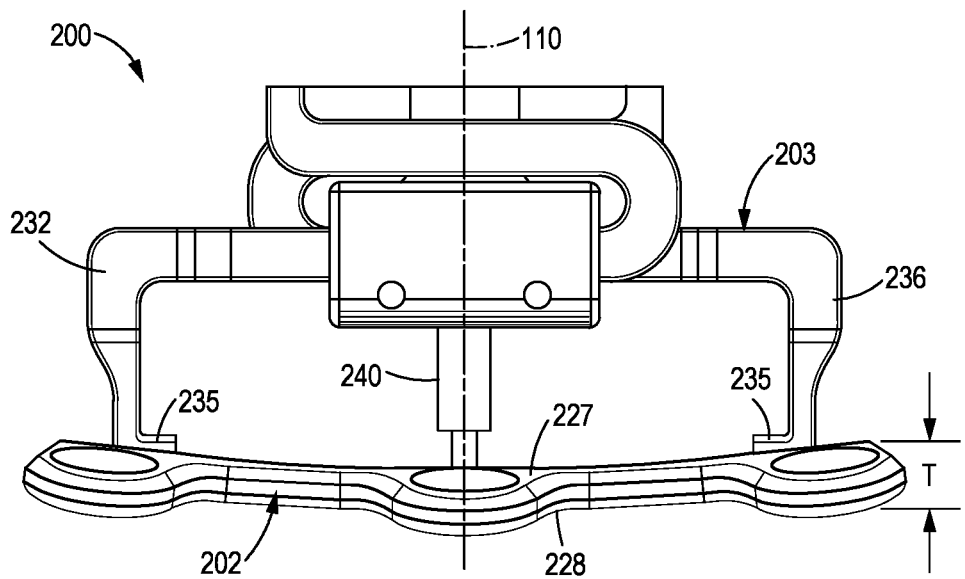
FIG. 12 is a side elevation view of a second example of a bone fixation system, including the surgical plate of FIG. 11 and a second example of an insertion tool, according to the present disclosure.

Next, the method 180 includes block 190 by positioning the surgical plate 102, while in the flexed shape, adjacent the bone 101, as best shown in FIG. 6. At block 192, the surgical plate 102 is coupled to the bone with fasteners 199 while the insertion tool 103 still holds the surgical plate 102 in the flexed shape, as best shown at FIG. 7. At block 194, the method 180 continues by moving the rod 140 along the vertical axis 110 from the second rod position to the first rod position, so that the shape memory material causes the surgical plate 102 to apply compression to the bone 101. At this point, the insertion tool 103 may be removed from the surgical plate 102 (block 196).

FIGS. 11-13A illustrate a second example of a bone fixation system 200 and method according to the present disclosure. The bone fixation system 200 is similar to the bone fixation system 100 illustrated in FIGS. 1-10, however a surgical plate 202 and insertion tool 203 are configured such that the insertion tool 203 pulls a plate body central portion 228 of the surgical plate 202 upward along the vertical axis 110 to place the surgical plate 202 in the flexed shape.

Figure 13A:
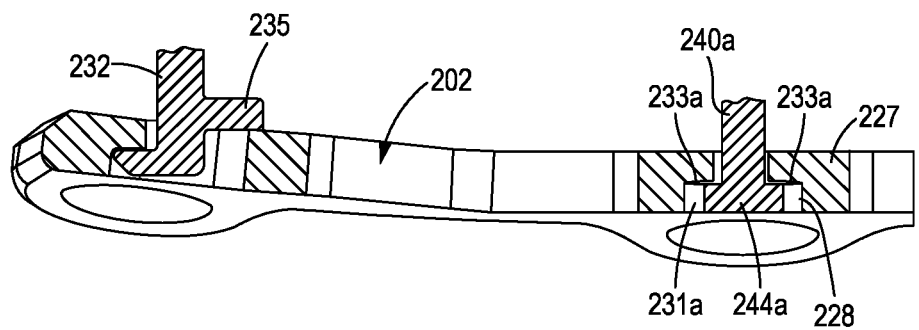
FIG. 13A is an enlarged side elevation view, in cross-section, of the bone fixation system of FIG. 12, with an arm of the insertion tool engaging a receptacle of the surgical plate, and with a rod of the insertion tool engaging a central aperture of the surgical plate.

More specifically in a first example, the plate body central portion 228 of the surgical plate 202 defines a central aperture 231a extending from an outward surface 227 to an inward surface 229 of the surgical plate 202 (FIG. 13A). Additionally, the insertion tool 203 includes a rod 240a configured to extend at least partially through the central aperture 231a. In the example shown at FIG. 13a, the rod 240a includes an eccentric head 244a. The rod 240a is rotatable between a first position, in which the eccentric head 244a is oriented to pass through the central aperture 231a, and a second position, in which the eccentric head 244a engages shoulders 233a of the central aperture 231a. In this example, each of the first and second arms 232, 236 of the insertion tool 203 may include a toe 235 configured to engage the outward surface 227 of the surgical plate 202.

Figure 13B:
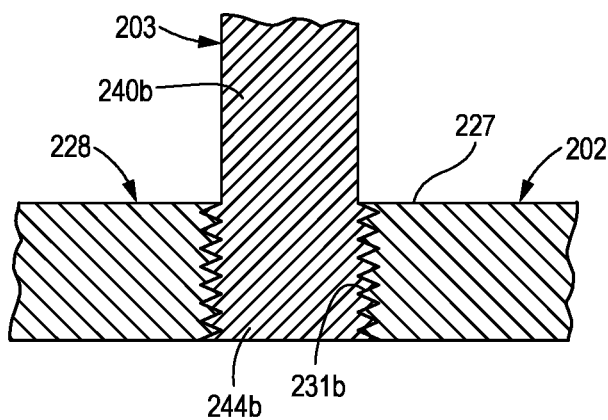
FIG. 13B is an enlarged side elevation view, in cross-section, of the bone fixation system of FIG. 12, with a rod of the insertion tool threadably engaging a threaded central aperture of the surgical plate.

In an alternative illustrated at FIG. 13B, the insertion tool 203 threadably engages the surgical plate 202. More specifically, the plate body central portion 228 of the surgical plate 202 defines a threaded central aperture 231b extending at least partially through the surgical plate 202 from the outward surface 227 toward the inward surface 229. The insertion tool 203 includes a rod 240b having a threaded end 244b configured to threadably engage the threaded central aperture 231b. As the rod 240b may be lowered until the threaded end 244b engages an entrance to the threaded central aperture 231b, at which time the rod 240b may be rotated so that the threaded end 244b advances into and threadably engages with the threaded central aperture 231b.

The bone fixation system 200 may be used to execute a method for fixating bone similar to the method 180 described above, however the plate body central portion 228 is raised upwardly in the flexed position, rather than lowered downwardly as in the example of FIGS. 1-10.

FIGS. 14-20 illustrate a third example of a bone fixation system 300 and method according to the present disclosure. The bone fixation system 300 is similar to the bone fixation systems 100, 200 described above, however a surgical plate 302 and insertion tool 303 are configured such that the insertion tool 303 both bends and elongates the surgical plate 302 prior to attachment to the bone 101.

Figure 14:
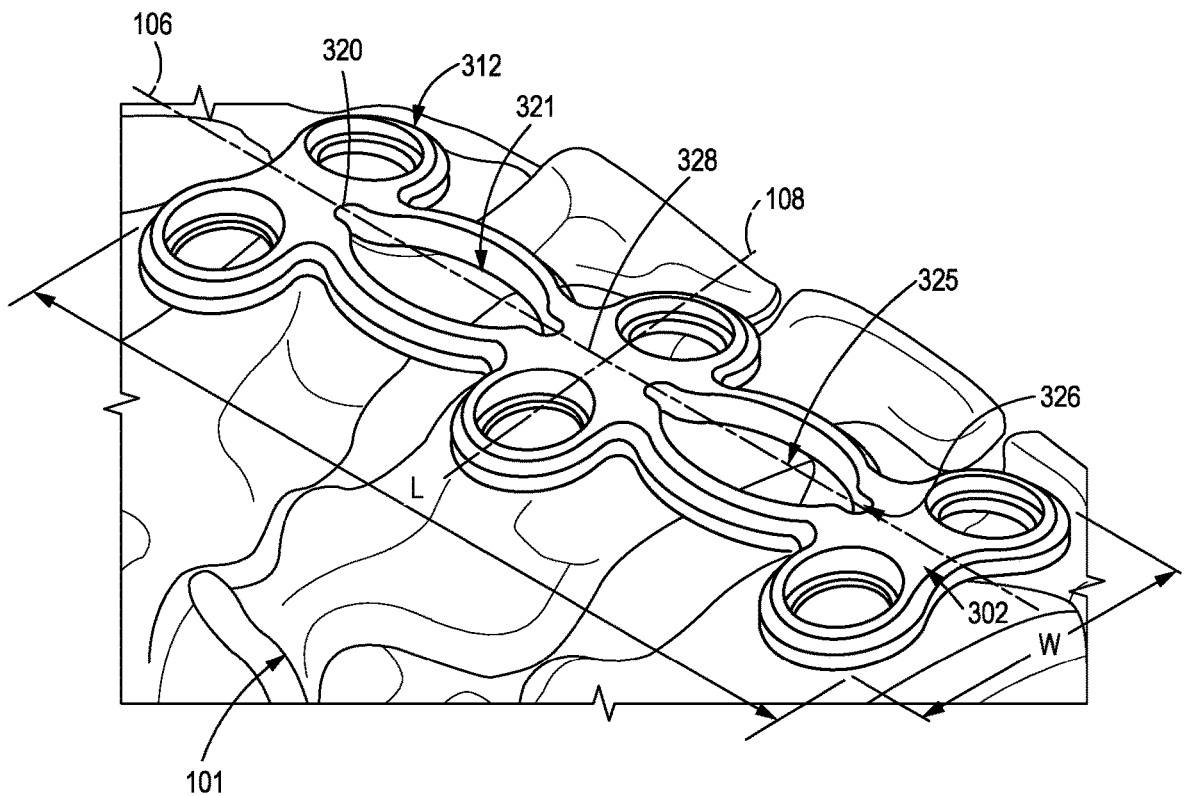
FIG. 14 is a perspective view of a third example of a surgical plate, according to the present disclosure, positioned adjacent to bone.
Figure 15:
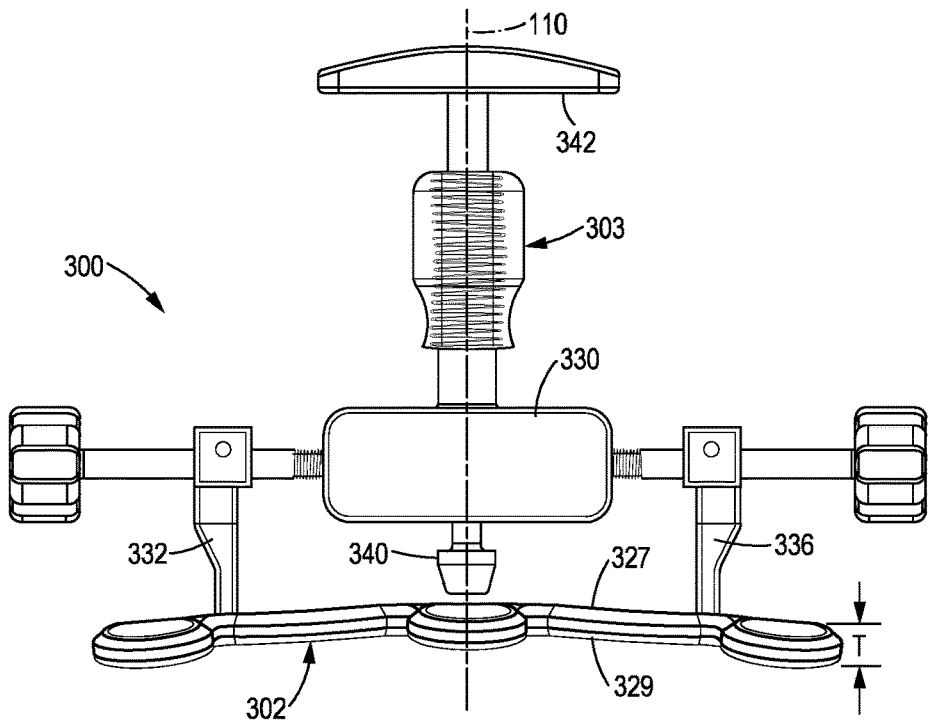
FIG. 15 is a side elevation view of a third example of a bone fixation system, including the surgical plate of FIG. 14 and a third example of an insertion tool, according to the present disclosure, with a rod of the insertion tool in a first position spaced from the surgical plate, and with the surgical plate in an initial shape.

The surgical plate 302 includes a plate body 304. As best shown in FIGS. 14 & 15, the plate body 304 spans a length L along the longitudinal axis 106, a width W along the lateral axis 108, and a thickness T along the vertical axis 110. The plate body 304 further defines a plate outer periphery 312 which defines the outer margins of the surgical plate 302 in the longitudinal and lateral axes 306, 308.

Figure 16:
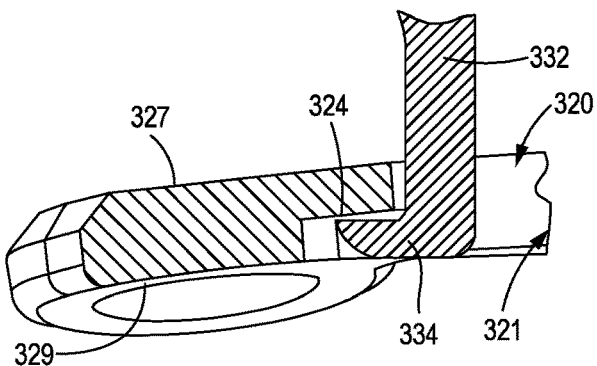
FIG. 16 is an enlarged side elevation view, in cross-section, of the bone fixation system of FIG. 15, with an arm of the insertion tool engaging a receptacle of the surgical plate.
Figure 17:
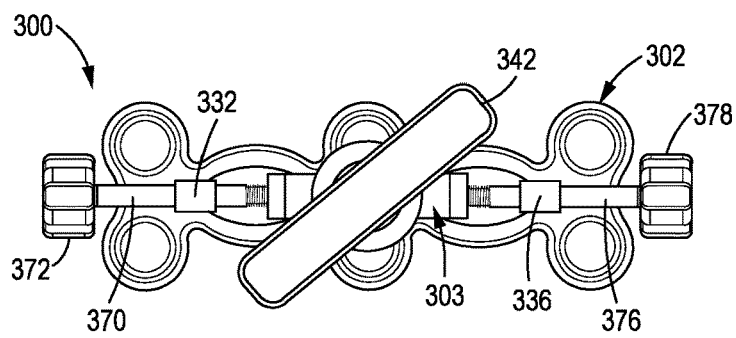
FIG. 17 is a top view of the bone fixation system of FIG. 15.

The surgical plate 302 includes areas for selective engagement with the insertion tool 303. As best shown in FIGS. 14-16, the surgical plate 302 includes a first receptacle 320 located inwardly of the plate outer periphery 312 and defining a first engagement point for the insertion tool 303. In the illustrated example, the first receptacle 320 is formed by a portion of a first access aperture 321 extending through the surgical plate 302, and defines a shoulder 324. The surgical plate 302 also includes a second receptacle 326, spaced from the first receptacle 320, which is located inwardly of the plate outer periphery 312 and defines a second engagement point for the insertion tool 303. The second receptacle 326 is formed by a portion of a second access aperture 325 extending through the surgical plate 302, and the second receptacle 326 also may define a shoulder 324. Accordingly, in contrast to the examples illustrated in FIGS. 1-13, the first and second receptacles 320, 326 in this example are not additional slots formed in the surgical plate for the dedicated purpose of providing engagement points for the insertion tool. Instead the first and second receptacles 320, 326 are formed by portions of apertures that provide additional functionality for the surgical plate 302, namely to provide access through the surgical plate 302 when positioned on the bone 101.

Still further, the surgical plate 302 includes a plate body central portion 328 located inwardly of the plate outer periphery 312 and disposed between the first and second receptacles 320, 326, the plate body central portion 328 defining a third engagement point for the insertion tool 303. The plate body central portion 328 defines an outward surface 327 and an inward surface 329 opposite the outward surface 327 and facing bone 101.

The insertion tool 303 engages and manipulates the surgical plate 302 as the surgical plate 302 is fixed to the bone 101. As illustrated in FIGS. 15-19, the insertion tool 303 includes a chassis 330. A first arm 332 is coupled to the chassis 330, and includes a first arm end 334 configured to engage the first receptacle 320. More specifically, as best shown in FIG. 16, the first arm 332 is sized to pass through the first receptacle 320, and the first arm end 334 is configured to engage the shoulder 324 of the first receptacle 320. The insertion tool 303 also includes a second arm 336 coupled to the chassis 330 configured to engage the second receptacle 326. While not illustrated separately, the second arm 336 may engage the second receptacle 326 in a manner similar to how the first arm 332 engages the first receptacle 320. In the illustrated example, each of the first and second arms 332, 336 is a rigid, structural component. The insertion tool 303 further includes a rod 340 coupled to the chassis 330 and disposed between first and second arms 332, 336.

The insertion tool 303 may be used to apply a three-point bend on the surgical plate 302, thereby to move the surgical plate 302 from an initial shape to a flexed shape. More specifically, with the first arm 332 of the insertion tool 303 engaging the first receptacle 320 of the surgical plate 302, and with the second arm 336 of the insertion tool 303 engaging the second receptacle 326 of the surgical plate 302, the rod 340 of the insertion tool 303 may be moved along the vertical axis 110 between a first rod position illustrated in FIG. 15, in which the rod 340 does not engage the surgical plate 302 and the surgical plate 302 has an initial shape, and a second rod position illustrated in FIG. 18, in which the rod 340 engages and displaces the plate body central portion 328 so that the surgical plate 302 has a flexed shape different from the initial shape. In this example, the rod 340 may be threadably coupled to the chassis 330. A knob 342 coupled to the rod 340 allows a user to manually rotate the rod 340, thereby to move the rod 340 along the vertical axis 110. In the example illustrated in FIGS. 15-18, the insertion tool 303 is configured to engage the outward surface 327 of the plate body central portion 328.

The first arm 332 also may be movable relative to the second arm 336 along the longitudinal axis 106. As best shown in FIGS. 15 and 17-19, The first arm 332 is coupled to a first threaded rod 370. One end of the first threaded rod 370 is threadably coupled to the chassis 330, while a knob 372 is coupled to the opposite end of the first threaded rod 370. Accordingly, rotation of the first threaded rod 370 will move the first arm 332 along the longitudinal axis 106, relative to the second arm 336.

In this example, the second arm 336 is also movable along the longitudinal axis 106. Accordingly, the second arm 336 is coupled to a second threaded rod 376. One end of the second threaded rod 376 is threadably coupled to the chassis 330, while a knob 378 is coupled to the opposite end of the second threaded rod 376. Accordingly, rotation of the second threaded rod 376 will move the second arm 336 along the longitudinal axis 106.

By moving at least the first arm 332 along the longitudinal axis 106, a distance between the first and second arms 332, 336 can be changed. For example, the first arm 332 may be movable relative to the second arm 336 between a first position, in which the first arm 332 and the second arm 336 are separated by a first longitudinal distance, and a second position, in which the first arm 332 and the second arm 336 are separated by a second longitudinal distance that is different from the first longitudinal distance. In some examples, the first longitudinal distance is less than the second longitudinal distance. In other examples, the first longitudinal distance is greater than the second longitudinal distance.

Figure 19:
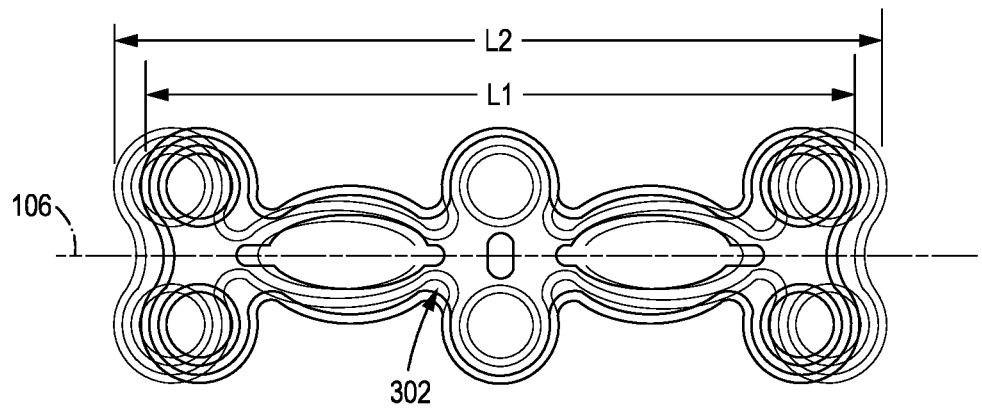
FIG. 19 illustrates juxtaposed top views of the surgical plate of FIG. 14 having an initial length and an extended length.
Figure 20:
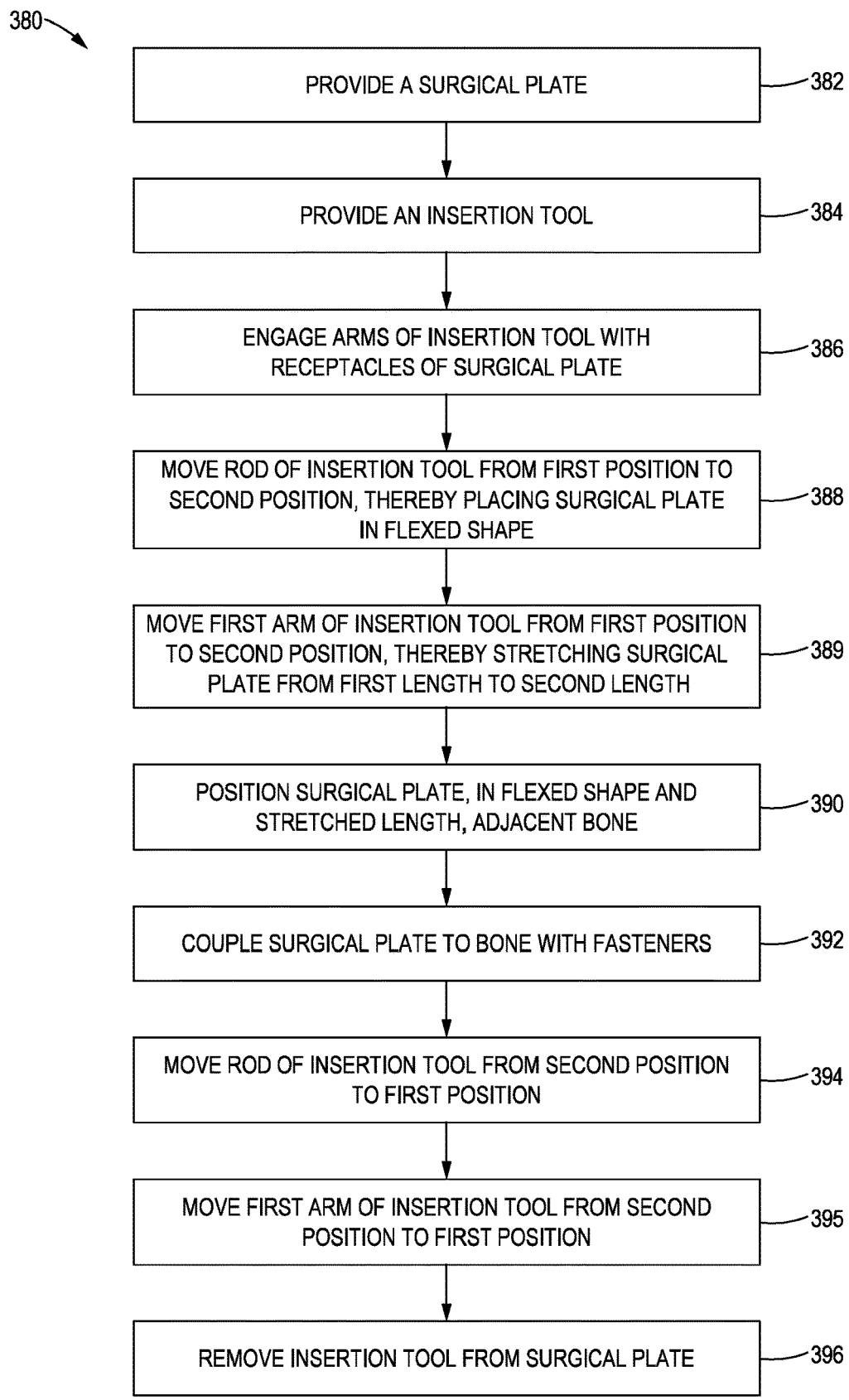
FIG. 20 is a block diagram of a method of fixating bone using the bone fixation system of FIG. 15.

Furthermore, adjusting the distance between the first and second arms 332, 336 allows the surgical plate 302 to be stretched along the longitudinal axis 106. More specifically, with the first arm 332 of the insertion tool 303 engaging the first receptacle 320 and the second arm 336 of the insertion tool 303 engaging the second receptacle 326, the surgical plate 302 will have a first length L1 when the first arm 332 is in the first position, and a second length L2, different from the first length L1, when the first arm 332 is in the second position, as best shown in FIG. 19. In this example, the first longitudinal distance is less than the second longitudinal distance, so that the first length L1 of the surgical plate 302 is less than the second length L2 of the surgical plate 302. In other examples, the first longitudinal distance may be greater than the second longitudinal distance, so that the first length L1 of the surgical plate 302 is greater than the second length L2 of the surgical plate.

Figure 18:
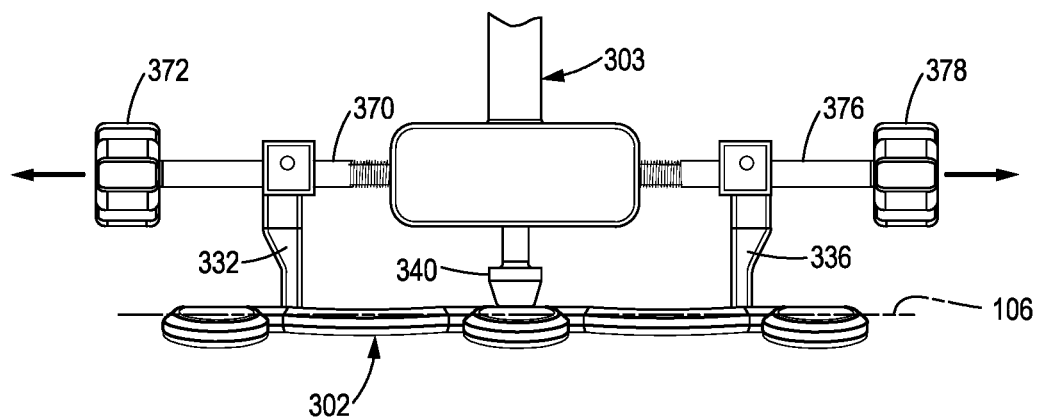
FIG. 18 is a side elevation view of the bone fixation system of FIG. 15, with the rod of the insertion tool in a second position that engages and deforms the surgical plate to a flexed shape, and with first and second arms of the insertion tool moved outwardly to extend a length of the surgical plate along a longitudinal axis.

FIGS. 15-20 illustrate a method 380 for fixating bone 101. The method 380 includes, at block 382, providing the surgical plate 302 described above and, at block 384, providing the insertion tool 303 described above. The method 380 continues with block 386, in which the first arm 332 of the insertion tool 303 is placed into engagement with the first receptacle 320 of the surgical plate 302 and the second arm 336 of the insertion tool 303 is placed into engagement with the second receptacle 326 of the surgical plate 302, as shown in FIG. 15. At block 388, the method continues by moving the rod 340 along the vertical axis 110 from a first rod position, in which the surgical plate 302 has an initial shape, to a second rod position, in which the rod 340 engages and displaces the plate body central portion 328 so that the surgical plate 302 has a flexed shape different from the initial shape, as best shown in FIG. 18. The method 380 continues at block 389, in which the first arm 332 is moved from the first position, in which the surgical plate 302 has the first length L1, to the second position, in which the surgical plate 302 has the second length L2. Alternatively, both the first and second arms 332, 336 may be moved to change the length of the surgical plate 302. It will be appreciated that the steps illustrated in blocks 388 and 389 may be reversed, such that the first arm 332 is moved to the second position before the rod 340 is moved to the second position. Still further, the steps illustrated in blocks 388 and 389 may be performed simultaneously Next, the method 380 includes block 390 of positioning the surgical plate 302, while in the flexed shape and with the elongated second length L2, adjacent the bone 101. 6. At block 392, the surgical plate 302 is coupled to the bone 101 with fasteners 399, while the insertion tool 303 still holds the surgical plate 302 in the flexed shape and with the second length L2. At block 394, the method 380 continues by moving the rod 340 along the vertical axis 110 from the second rod position to the first rod position, so that the shape memory material causes the surgical plate 302 to apply compression to the bone. Additionally, at block 395, the first arm 332 is moved from the second position to the first position, thereby to cause the surgical plate 302 to apply additional force to the bone. It will be appreciated that the steps illustrated in blocks 394 and 395 may be reversed, such that the first arm 332 is returned to the first position before the rod 340 is returned to the first position. Still further, the steps illustrated in blocks 394 and 395 may be performed simultaneously. Finally, at block 396, the insertion tool 303 may be removed from the surgical plate 302 (block 396).

Figure 21:
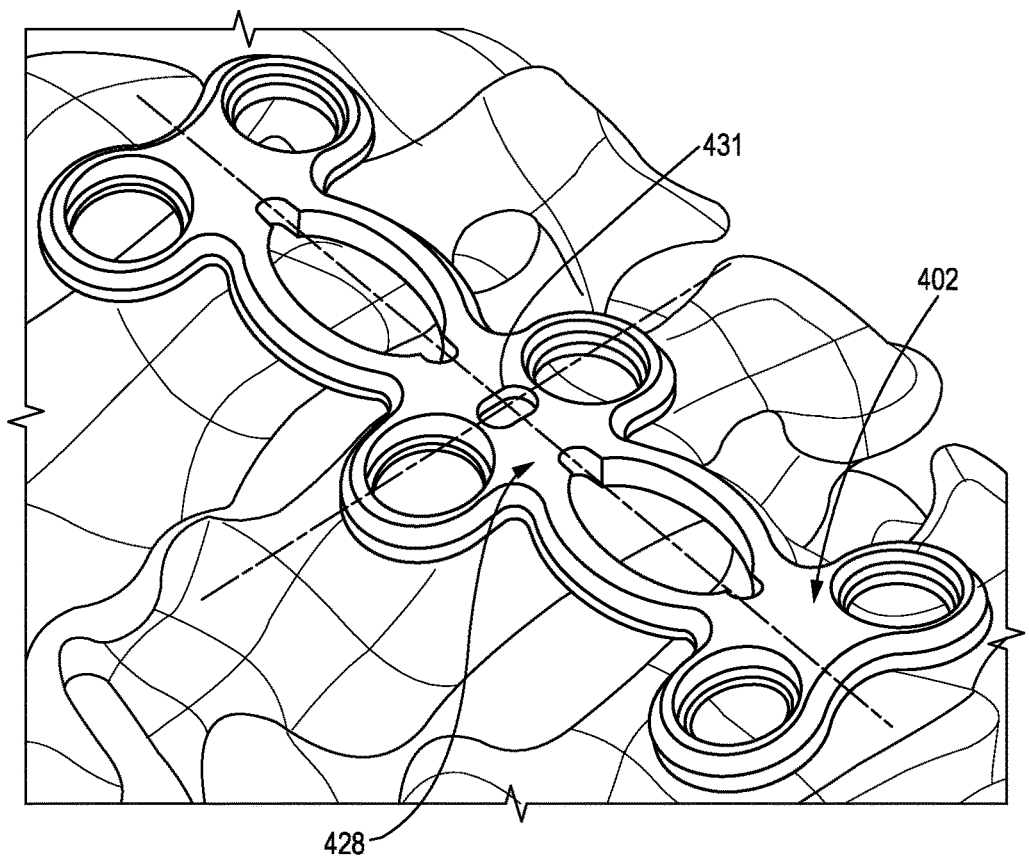
FIG. 21 is a perspective view of a fourth example of a surgical plate, according to the present disclosure, positioned adjacent to bone.
Figure 22:
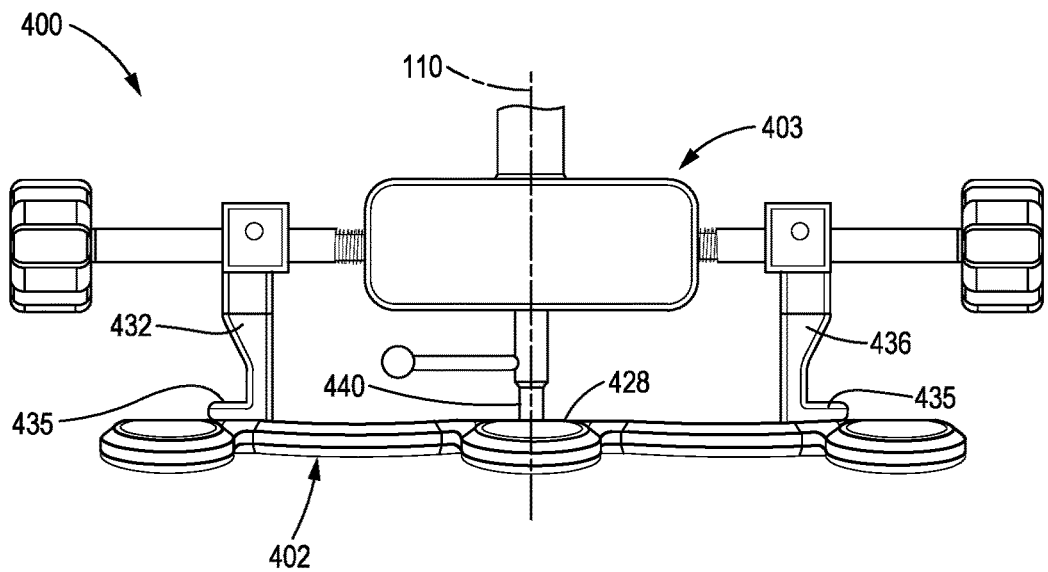
FIG. 22 is a side elevation view of a fourth example of a bone fixation system, including the surgical plate of FIG. 21 and a fourth example of an insertion tool, according to the present disclosure, with a rod of the insertion tool in a second position that engages and deforms the surgical plate to a flexed shape, and with first and second arms of the insertion tool moved outwardly to extend a length of the surgical plate along a longitudinal axis.
Figure 23:
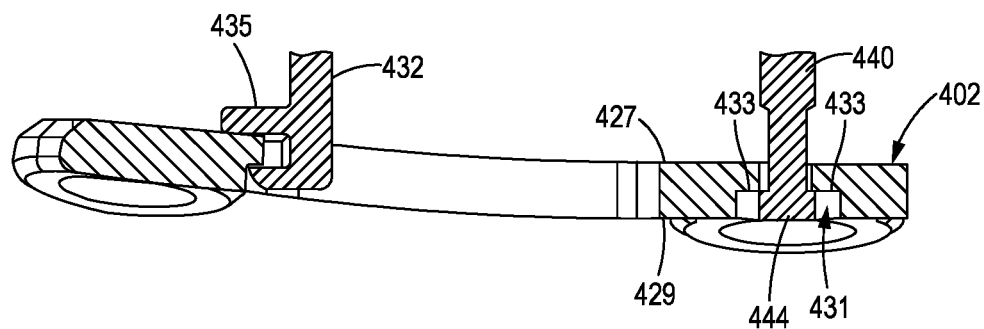
FIG. 23 is an enlarged side elevation view, in cross-section, of the bone fixation system of FIG. 21, with an arm of the insertion tool engaging a receptacle of the surgical plate, and with a rod of the insertion tool engaging a central aperture of the surgical plate.

FIGS. 21-23 illustrate a fourth example of a bone fixation system 400 and method according to the present disclosure. The bone fixation system 400 is similar to the bone fixation system 300 illustrated in FIGS. 14-20, however a surgical plate 402 and insertion tool 403 are configured such that the insertion tool 403 pulls a plate body central portion 428 of the surgical plate 402 upward along the vertical axis 110 to place the surgical plate 402 in the flexed shape.

More specifically, the plate body central portion 428 of the surgical plate 402 defines a central aperture 431 extending from an outward surface 427 to an inward surface 429 of the surgical plate 402. Additionally, the insertion tool 403 includes a rod 440 configured to extend at least partially through the central aperture 431. The rod 440 is configured to engage the central aperture 431 or the inward surface 429 of the plate body central portion 428. In the example shown at FIG. 23, the rod 440 includes an eccentric head 444. The rod 440 is rotatable between a first position, in which the eccentric head 444 is oriented to pass through the central aperture 431, and a second position, in which the eccentric head 444 engages shoulders 433 of the central aperture 431. Alternatively, the central aperture 431 and the rod 440 may be threaded, with the rod 440 threadably engaging the central aperture 431, as described above with reference to FIG. 13B. Additionally, each of first and second arms 432, 436 of the insertion tool 403 may include a toe 435 configured to engage the outward surface 427 of the surgical plate 402.

The bone fixation system 400 may be used to execute a method for fixating bone similar to the method 380 described above, however the plate body central portion 428 is raised upwardly in the flexed position, rather than lowered downwardly as in the example of FIGS. 14-20.

All references, including publications, patent applications, and patents, cited herein are hereby incorporated by reference. The description of certain embodiments as "preferred" embodiments, and other recitation of embodiments, features, or ranges as being preferred, is not deemed to be limiting, and the claims are deemed to encompass embodiments that may presently be considered to be less preferred. All methods described herein can be performed in any suitable order unless otherwise indicated herein or otherwise clearly contradicted by context. The use of any and all examples, or exemplary language (e.g., "such as") provided herein, is intended to illuminate the disclosed subject matter and does not pose a limitation on the scope of the claims. Any statement herein as to the nature or benefits of the exemplary embodiments is not intended to be limiting, and the appended claims should not be deemed to be limited by such statements. More generally, no language in the specification should be construed as indicating any non-claimed element as being essential to the practice of the claimed subject matter. The scope of the claims includes all modifications and equivalents of the subject matter recited therein as permitted by applicable law. Moreover, any combination of the above-described elements in all possible variations thereof is encompassed by the claims unless otherwise indicated herein or otherwise clearly contradicted by context. The description herein of any reference or patent, even if identified as "prior," is not intended to constitute a concession that such reference or patent is available as prior art against the present disclosure.

What is claimed is:

1. A bone fixation system, comprising:
   a surgical plate formed of a shape memory material, the surgical plate comprising:
   a plate body spanning a length along a longitudinal axis, a width along a lateral axis perpendicular to the longitudinal axis, and a thickness along a vertical axis orthogonal to both the longitudinal axis and the lateral axis, the plate body defining a plate outer periphery, an outward surface and an inward surface opposite the outward surface and facing a bone when the surgical plate is fixed to the bone;
   a first receptacle located inwardly of the plate outer periphery and having a first shoulder;
   a second receptacle located inwardly of the plate outer periphery, having a second shoulder, and spaced from the first receptacle; and
   a plate body central portion located inwardly of the plate outer periphery and disposed between the first and second receptacles; and an insertion tool, comprising:
- a first arm having a first arm end configured to engage the first shoulder of the first receptacle without extending past the inward surface;
- a second arm having a second arm end configured to engage the second shoulder of the second receptacle without extending past the inward surface; and
- a rod disposed between the first and second arms and configured to engage the plate body central portion, the rod supported for movement along the vertical axis; and wherein, with the first arm end of the insertion tool engaging the first shoulder of the surgical plate and the second arm end of the insertion tool engaging the second shoulder of the surgical plate, the rod of the insertion tool is movable along the vertical axis between a first rod position, in which the surgical plate has an initial shape, and a second rod position, in which the rod engages and displaces the plate body central portion so that the surgical plate has a flexed shape different from the initial shape.

2. The bone fixation system of claim 1, wherein the plate body central portion defines an outward surface and an inward surface opposite the outward surface.

3. The bone fixation system of claim 2, wherein the rod of the insertion tool is configured to engage the outward surface of the plate body central portion.

4. The bone fixation system of claim 2, wherein:
the plate body central portion defines a central aperture extending from the outward surface to the inward surface; and
the rod extends at least partially through the central aperture and engages the central aperture or the inward surface of the plate body central portion.

5. The bone fixation system of claim 1, wherein:
the first arm is movable relative to the second arm along the longitudinal axis between a first position, in which the first arm and the second arm are separated by a first longitudinal distance, and a second position, in which the first and second arm are separated by a second longitudinal distance that is different from the first longitudinal distance; and
with the first arm of the insertion tool engaging the first receptacle and the second arm of the insertion tool engaging the second receptacle, the surgical plate has a first length when the first arm is in the first position, and a second length, different from the first length, when the first arm is in the second position.

6. The bone fixation system of claim 5, wherein the first longitudinal distance is less than the second longitudinal distance, so that the first length of the surgical plate is less than the second length of the surgical plate.

7. The bone fixation system of claim 1, wherein the shape memory material comprises nitinol.

8. The bone fixation system of claim 1, wherein each of the first and second arms comprises a rigid, structural component.

9. The bone fixation system of claim 1, wherein plate body includes a first slot defining the first receptacle, and a second slot defining the second receptacle.

10. The bone fixation system of claim 1, wherein the plate body includes a first access aperture defining the first receptacle, and a second access aperture defining the second receptacle.

11. A method for fixating bone, the method comprising:
providing a surgical plate formed of a shape memory material, the surgical plate comprising:
- a plate body spanning a length along a longitudinal axis, a width along a lateral axis perpendicular to the longitudinal axis, and a thickness along a vertical axis orthogonal to both the longitudinal axis and the lateral axis, the plate body defining a plate outer periphery;
- a first receptacle located inwardly of the plate outer periphery;
- a second receptacle located inwardly of the plate outer periphery and spaced from the first receptacle; and
- a plate body central portion located inwardly of the plate outer periphery and disposed between the first and second receptacles; and providing an insertion tool, comprising:
- a first arm configured to engage the first receptacle;
- a second arm configured to engage the second receptacle; and
- a rod disposed between the first and second arms and configured to engage the plate body central portion, the rod supported for movement along the vertical axis;

engaging the first arm of the insertion tool with the first receptacle of the surgical plate;
engaging the second arm of the insertion tool with the second receptacle of the surgical plate;
moving the rod along the vertical axis from a first rod position, in which the surgical plate has an initial shape, to a second rod position, in which the rod engages and displaces the plate body central portion so that the surgical plate has a flexed shape different from the initial shape;
positioning the surgical plate, while in the flexed shape, adjacent the bone;
securing the surgical plate to the bone with fasteners, wherein the fasteners are screws that are inserted through openings through the plate body and screwed into the bone; and
moving the rod along the vertical axis from the second rod position to the first rod position, so that the shape memory material causes the surgical plate to apply compression to the bone.

12. The method of claim 11, wherein the first arm is movable relative to the second arm along the longitudinal axis between a first position, in which the first arm and the second arm are separated by a first longitudinal distance, and a second position, in which the first and second arm are separated by a second longitudinal distance that is different from the first longitudinal distance, the method further comprising:
prior to positioning the surgical plate adjacent the bone, and with the first arm of the insertion tool engaging the first receptacle and the second arm of the insertion tool engaging the second receptacle, moving the first arm from the first position, in which the surgical plate has a first length, to the second position, in which the surgical plate has a second length, different from the first length; and
after securing the surgical plate to the bone with fasteners, moving the first arm from the second position to the first position to cause the surgical plate to apply additional compression to the bone.

13. The method of claim 12, wherein the first longitudinal distance is less than the second longitudinal distance, so that the first length of the surgical plate is less than the second length of the surgical plate.

14. The method of claim 11, wherein the plate body central portion defines an outward surface and an inward surface opposite the outward surface.

15. The method of claim 14, wherein the rod of the insertion tool is configured to engage the outward surface of the plate body central portion as the rod moves between the first rod position and the second rod position.

16. The method of claim 14, wherein:
the plate body central portion defines a central aperture extending from the outward surface to the inward surface; and
the rod extends at least partially through the central aperture and engages the central aperture or the inward surface of the plate body central portion as the rod moves between the first rod position and the second rod position.

17. The method of claim 11, wherein the shape memory material comprises nitinol.

18. The method of claim 11, wherein each of the first and second arms comprises a rigid, structural component.

19. The method of claim 11, wherein the plate body includes a first access aperture defining the first receptacle, and a second access aperture defining the second receptacle.

20. A bone fixation system, comprising:
a surgical plate formed of nitinol, the surgical plate comprising:
  a plate body spanning a length along a longitudinal axis, a width along a lateral axis perpendicular to the longitudinal axis, and a thickness along a vertical axis orthogonal to both the longitudinal axis and the lateral axis, the plate body defining a plate outer periphery, an outward surface and an inward surface opposite the outward surface and facing a bone when the surgical plate is fixed to the bone;
  a first receptacle located inwardly of the plate outer periphery and having a first shoulder;
  a second receptacle located inwardly of the plate outer periphery, having a second shoulder, and spaced from the first receptacle; and
  a plate body central portion located inwardly of the plate outer periphery and disposed between the first and second receptacles; and
an insertion tool, comprising:
  a first arm having a first arm end configured to engage the first shoulder of the first receptacle without extending past the inward surface;
  a second arm having a second arm end configured to engage the second shoulder of the second receptacle without extending past the inward surface; and
  a rod disposed between the first and second arms and configured to engage the plate body central portion, the rod supported for movement along the vertical axis;
wherein, with the first arm end of the insertion tool engaging the first shoulder of the surgical plate and the second arm end of the insertion tool engaging the second shoulder of the surgical plate, the rod of the insertion tool is movable along the vertical axis between a first rod position, in which the surgical plate has an initial shape, and a second rod position, in which the rod engages and displaces the plate body central portion so that the surgical plate has a flexed shape different from the initial shape;
wherein the first arm is movable relative to the second arm along the longitudinal axis between a first position, in which the first arm and the second arm are separated by a first longitudinal distance, and a second position, in which the first and second arm are separated by a second longitudinal distance that is less than the first longitudinal distance; and
wherein, with the first arm of the insertion tool engaging the first receptacle and the second arm of the insertion tool engaging the second receptacle, the surgical plate has a first length when the first arm is in the first position, and a second length, less than the first length, when the first arm is in the second position.

* * * * *